United States Patent [19]
Furumoto et al.

[11] Patent Number: 5,843,072
[45] Date of Patent: Dec. 1, 1998

[54] METHOD FOR TREATMENT OF UNWANTED VEINS AND DEVICE THEREFOR

[75] Inventors: Horace W. Furumoto, Wellesley; George Cho, Hopkinton, both of Mass.; David H. McDaniel, Virginia Beach, Va.

[73] Assignee: Cynosure, Inc., Chelmsford, Mass.

[21] Appl. No.: 745,133

[22] Filed: Nov. 7, 1996

[51] Int. Cl.⁶ .................................................. A61B 17/36
[52] U.S. Cl. .................................. 606/9; 606/10; 606/12
[58] Field of Search ................................. 604/20; 606/9, 606/10, 12; 128/898

[56] References Cited

U.S. PATENT DOCUMENTS

| | | | |
|---|---|---|---|
| 3,693,623 | 9/1972 | Harte et al. | 128/303.1 |
| 3,769,963 | 11/1973 | Goldman et al. | 128/2 R |
| 4,461,294 | 7/1984 | Baron | 128/303.1 |
| 5,057,104 | 10/1991 | Chess | 606/9 |
| 5,071,416 | 12/1991 | Heller, et al. | 606/3 |
| 5,290,273 | 3/1994 | Tan | 606/9 |
| 5,344,418 | 9/1994 | Ghaffari | 606/9 |
| 5,423,800 | 6/1995 | Ren et al. | 606/4 |
| 5,527,350 | 6/1996 | Grove et al. | 607/89 |
| 5,558,666 | 9/1996 | Dewey et al. | 606/9 |
| 5,558,667 | 9/1996 | Yarborough et al. | 606/9 |
| 5,578,029 | 11/1996 | Trelles et al. | 606/25 |
| 5,658,323 | 8/1997 | Miller | 607/89 |

FOREIGN PATENT DOCUMENTS

| | | | |
|---|---|---|---|
| 0 142 671 A1 | 5/1985 | European Pat. Off. | A61B 17/36 |
| 0 458 576 A2 | 11/1991 | European Pat. Off. | H01S 3/08 |
| 0 575 274 A1 | 12/1993 | European Pat. Off. | A61C 1/00 |
| WO 91/12050 | 8/1991 | WIPO | A61N 5/06 |
| WO 91/18646 | 12/1991 | WIPO | A61N 5/06 |
| WO 95/33518 | 12/1995 | WIPO | A61N 5/06 |
| WO 96/23447 | 8/1996 | WIPO | A61B 17/36 |

OTHER PUBLICATIONS

Goldman, M.P., "Leg Veins and Lasers", Abstract, American Society for Laser Medicine and Surgery, 14th Annual Meeting, Apr. 8–10, 1994.

"Hydrogel Dressings Contain Particles During Laser Therapy," *Dermatology Times 94–01, ISSN–01966197*, p. 26 (1994).

Goldman, M.P., "Sclerotherapy —Treatment of Varicose and Telangiectatic Leg Veins," *Second Edition, Mosby*, pp. 454–467 (No Date Given).

"Temperature Indicating Tab, Crayons, Lacquers, and Pellets," pp. F5–F6, F13, F19 (Advertisement Brochure —No Date Given).

Anderson, R.R., et al., Selective Photothermolysis: Precise Microsurgery by Selective Absorption of Pulsed Radiation, *Science*, vol. 220, pp. 524–527 (Apr. 29, 1983).

Anderson, R.R., et al., "The Optics of Human Skin," *The Journal of Investigative Dermatology*, 77:13–19 (1981).

*Primary Examiner*—Jennifer Bahr
*Assistant Examiner*—Roy Gibson
*Attorney, Agent, or Firm*—Hamilton, Brook, Smith & Reynolds, P.C.

[57] ABSTRACT

A combined sclerotherapy and light treatment method is described for the treatment of unwanted veins such as varicose and telangiectatic leg veins. Substantially increased success, in the range of 90–100%, has been achieved by implementing a dwell time of between 12 hours and 6 months between the light-based therapy and the sclerotherapy. Near infra-red wavelength light is preferably used in the light therapy due to its better depths of penetration through the skin to deeper lying, larger vessels such as varicose veins.

14 Claims, 6 Drawing Sheets

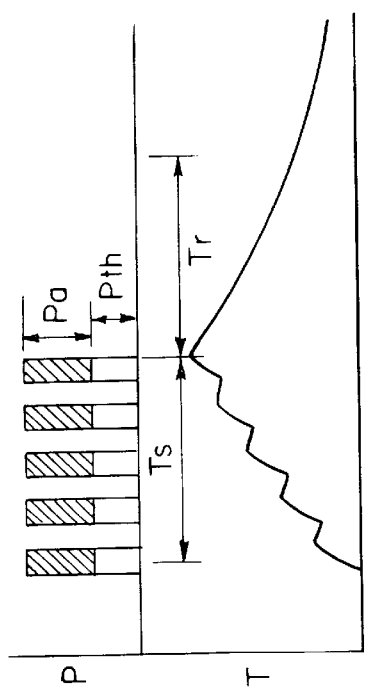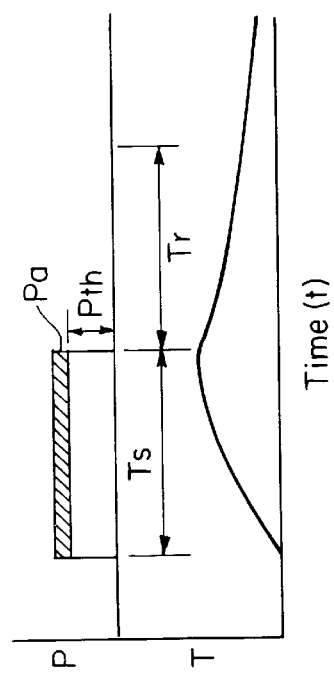

METHOD FOR TREATMENT OF UNWANTED VEINS AND DEVICE THEREFOR

RELATED APPLICATIONS

This application is related to U.S. Pat. application Ser. No. 08/744,344, filed Nov. 7, 1996, entitled "Alexandrite Laser System For Hair Removal And Method Therefor", by Horace W. Furumoto, et al., the teachings of which are incorporated herein by this reference in their entirety.

BACKGROUND OF THE INVENTION

Varicose and telangiectatic leg veins are common forms of ectatic vascularization. Varicose veins have been classified into three groups: dilated saphenous veins, dilated superficial branches and dilated venules. More encompassing classification for the conditions is simply unwanted leg veins. Light therapy, sclerotherapy, and vein stripping are typical modes of treating these conditions. Each therapy has its advantages and disadvantages.

Photocoagulation based on the principle of selective photothermolysis underlies most light therapies to treat leg veins. The dermal and epidermal layers containing the veins are irradiated with light, usually from lasers or flashlamps. The wavelength or color of this light is chosen so that its energy will be preferentially absorbed in the targeted veins. This leads to the localized heating of the veins with the intent of raising the temperature of the veins to a point at which the constituent proteins will denature. The pulse duration of the irradiating light is also important for selectivity. If the pulse duration is too long, heat absorbed by the veins will diffuse out into the surrounding tissues so that the veins will not be selectively heated to the degree necessary to selectively destroy only the veins. If the pulse durations are too short, however, the light absorbing chemical species such as blood hemoglobin will be heated too quickly causing vaporization. This effect can cause purpura. Theory dictates that the proper pulse width should match the thermal diffusion time of the targeted structures. For smaller vessels contained in portwine stain birthmarks, for example, these thermal diffusion times can be on the order of hundreds of microseconds ($\mu$sec) to several milliseconds (msec). Larger leg veins, however, can have thermal diffusion times in the 5 to 100 msec range.

Various types of lasers have been tested for the treatment of leg veins. Nd:YAG lasers (operating at 1060 nanometers (nm)), carbon dioxide (operating at 10.6 micrometers), and argon (operating in the 488–514 nm range) have been suggested for the treatment of telangiectatic veins. The consensus, however, seems to be that these lasers do not produce light that is selective for the targeted vessels. They tend to cause general tissue destruction that leads to scarring, pain, and hypo-, hyper-pigmentation. The most successful treatments have been achieved using dye lasers, and specifically flashlamp-excited pulse dye lasers (FLPDL). These lasers operate in the 577–585 nm range where there are absorption band peaks for hemoglobin and also operate well in the pulsed mode that provides for good selectivity. With the proper selection of color and pulse duration, success rates of higher than 50% are common when treating smaller telangiectatic veins. Unfortunately, dye lasers are limited in pulse durations to less than 1.5 milliseconds. Thus, they tend to be inappropriate for the treatment of larger varicose veins that would require pulse durations of hundreds of milliseconds, at least according to the principle. Attempts are being made to solve this problem. Frequency doubling Nd:YAG has been proposed as a technique to generate long pulses at 532 nm. See U.S. Pat. No. 5,558,667 to Yarborough, et al.

The alternative to laser or light treatment is sclerotherapy in which chemicals are injected into the vessels to destroy the vessels. A common sclerosing agent is, for example, hypertonic saline and dextrose. The ultimate success is highly dependent upon the success with which the sclerosing agent can be introduced into the vessels. The typical sclerotherapy involves placing multiple injections of the agent along the targeted veins to produce diffuse sclerosis. Accuracy can be increased with the use of ultrasound or doppler-guided injections and endoscopic injection procedures. With good surgical technique, success as high as 80% can be achieved, but success in the range of 60% is more common.

Approaches combining FLPDL treatments with sclerotherapy have also been proposed for treating leg telangiectasias. See *Sclerotherapy* by Goldman, Mitchell; Mosby (1995) at pages 454–458. The leg telangiectasias were treated with laser energy immediately before injection of a sclerosing agent. Generally, the study concluded that the increased complications associated with the combined treatment did not justify the small, if any, added benefit. Generally, it concluded that the combined treatment offered no advantage over FLPDL treatment alone.

SUMMARY OF THE INVENTION

The principal drawback associated with sclerotherapy and the light therapies is their limited success rates. While in many medical procedures, success rates of 60–80% would be acceptable, the treatment of varicose veins and telangiectatic veins is principally cosmetic in nature. Thus, even a slight risk of complications may advocate against the use of either therapy, and the lack of guaranteed success can tip the balance in favor of no treatment.

The present invention is directed to a combined sclerotherapy and light treatment method for unwanted veins. In this way, it is similar to FLPDL-sclerotherapy approach from the prior art. Substantially increased success, in the range of 90–100%, however, has been achieved by implementing a dwell time of between 12 hours and 6 months between the light-based therapy and the sclerotherapy. Preferably, the light-based therapy is performed before the sclerotherapy. Success can be achieved by performing the sclerotherapy followed by the light-based therapy after the dwell time, however.

Moreover, research suggests that the 577–585 nm range of the FLPDL is not optimal. Instead, it is desirable to use light in the 680–1,100 nm range, the near-infrared portion of the spectrum. It appears that light in the range of 577–585 is absorbed too efficiently by the dermal and epidermal structures. Near-infrared light achieves better depths of penetration through the skin to the vessels. This allows the treatment of deeper lying, larger vessels such as varicose veins. Further, since the near-infrared is also less efficiently absorbed in the vessels themselves, they are more uniformly heated across their cross-sections. Vessels larger than 0.5 millimeters (mm) can be treated at depths of greater than 1 mm. In contrast, the 577–585 range tends only to heat the vessel surfaces that face the light source.

In specific embodiments, an Alexandrite laser operating in the 755 nanometer range is a preferred light source, although flashlamp sources could also be used. There is enhanced absorption by reduced hemoglobin at 755 nm, which provides better blood absorption than ruby lasers operating at 694 nm. Further, the alexandrite laser can be pulsed at the optimum pulse duration and at the same time provide larger energy output and larger spot sizes for the required fluences. There is also enhanced absorption at 960 nm by oxyhemoglobin, but pulsed lasers at this wavelength do not provide an adequate energy output, under current technology.

Further, it is desirable to use pulse periodic heating techniques especially when using the alexandrite laser with pulse durations greater than 10 msec. These techniques rely on the use of a series of laser light pulses with a limited duty cycle that have a total duration of the thermal relaxation time of the targeted vessels. The total power of the pulses is that necessary to denature the targeted vessels. The pulse periodic heating technique efficiently uses the laser by reducing the absorption of energy needed to get to the laser threshold. This energy does not contribute to laser action and is lost.

According to another aspect, the invention also features a kit for the treatment of unwanted blood vessels. It comprises a light source for irradiating the vessels with light adapted to initiate destruction of the vessels. A sclerosing agent, such as a hypertonic saline solution, is also needed for injection into the vessels. Instructions are desirably provided with the light source that suggest waiting for a dwell time between the irradiation of the vessels and sclerosing agent injection.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 3A and 3B are power and temperature plots as a function of time for pulse periodic heating and constant amplitude heating, respectively.

DETAILED DESCRIPTION OF THE PREFERRED EMBODIMENTS

Figure 1A:
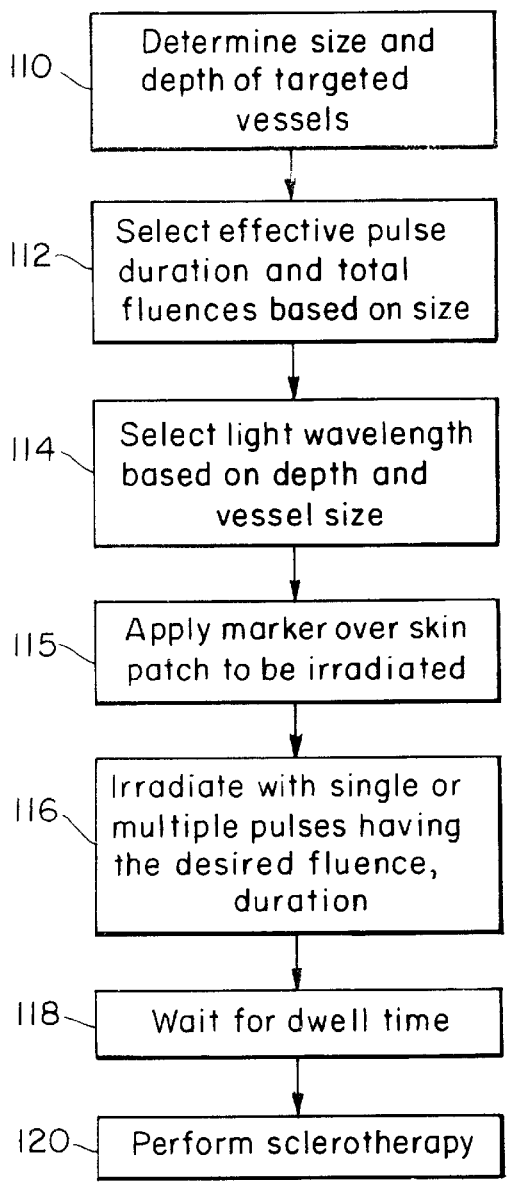
FIGS. 1A and 1B are process diagrams illustrating combined light and sclerotherapy techniques for treating leg veins according to the two embodiments of the present invention.
Figure 1B:
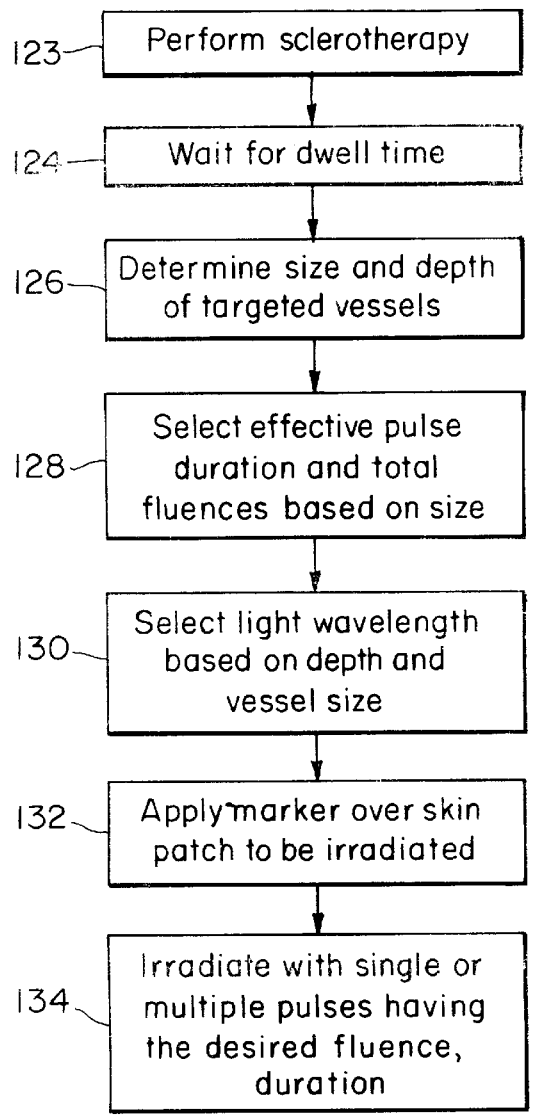

FIG. 1A shows a combined light and sclerotherapy technique implementing the principles of the present invention. Generally, the technique includes near-infrared irradiation of the targeted vessels followed by a dwell time in which the destructive effects of the light therapy are realized in the targeted vessels. After this time expires, sclerotherapy is performed on the vessels. Alternatively, the sclerotherapy could be performed first followed by the dwell time and then the near-infrared irradiation of the unwanted vessels as shown in FIG. 1B and discussed later.

In more detail, light therapy is first performed in steps 110–116. The first step in this process, step 110, is to assess the size and depth of the targeted varicose or telangiectatic leg veins. Generally an experienced physician can do this visually, although measuring devices may be used.

The size of the targeted vessels dictates the effective pulse duration and total fluence, in step 112. The pulse duration should ideally be closely matched to the thermal relaxation time of the vessels, and the thermal relaxation time is a function of the vessels size. Generally, for the treatment of the vessels such as varicose veins, total effective pulse durations of greater than a millisecond are desirable, with 5 milliseconds to 100 milliseconds being preferred in the case of larger vessels.

The total fluence, Joules per square centimeter ($J/cm^2$), is dictated also by the vessel's size. The fluence should be high enough to, over the course of the pulse duration, raise the walls of the vessel to a temperature at which their constituent proteins will denature. A temperature of 70° C. is an accepted target. In general, the total energy deposited is preferably greater than 5 $J/cm^2$, although fluences in the range of 15–30 $J/cm^2$ are more common with approximately 20 $J/cm^2$ preferred in most situations.

Figure 4:
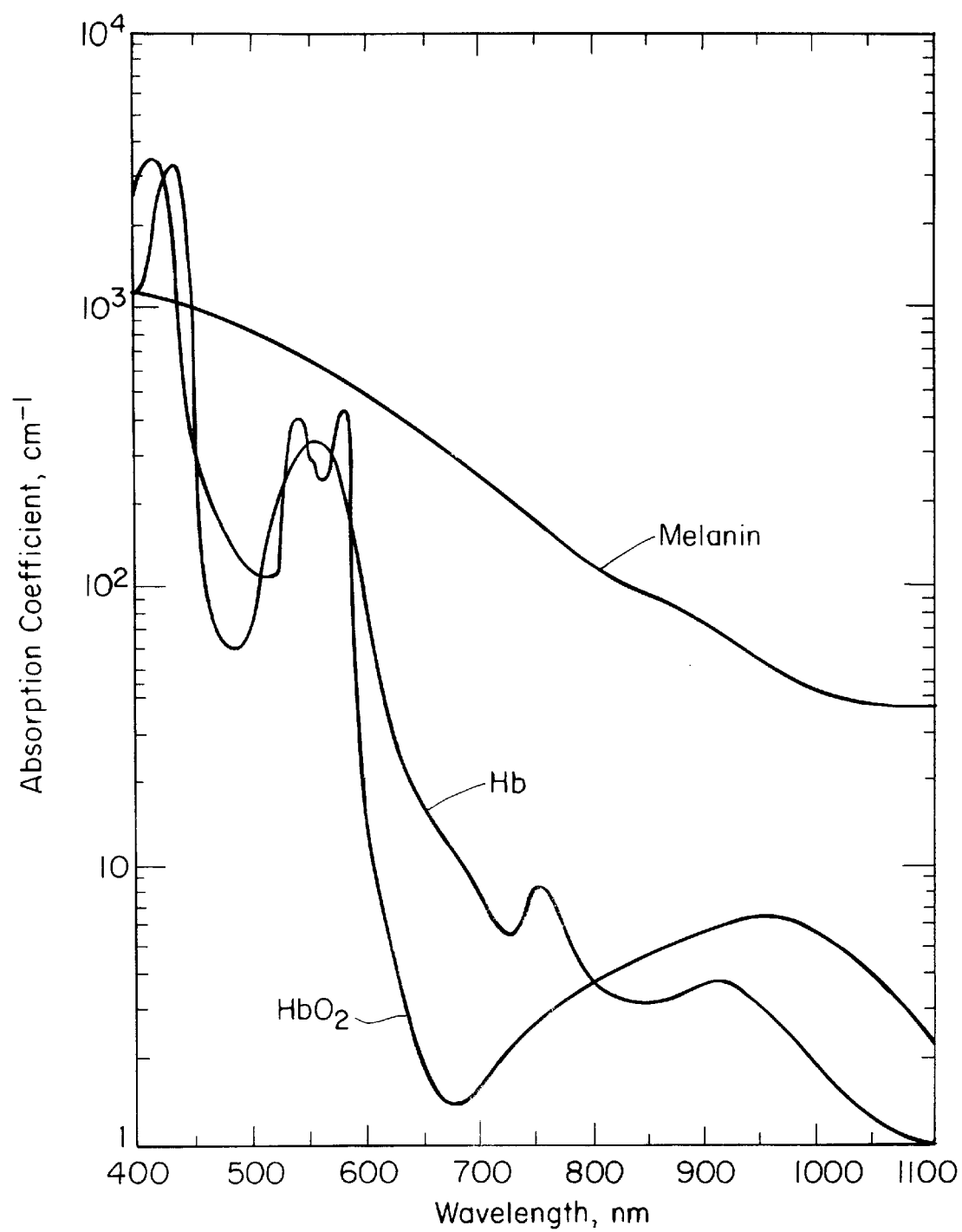
FIG. 4 is a plot of the spectral absorption of hemoglobin and melanin.

In step 114, the wavelength of the irradiating light is selected based upon the depth and size of the vessels. Generally, for smaller telangiectatic veins near the skin's surface, the desired wavelength is 577–585 nanometers. The limited penetration depth at this wavelength is not a substantial impediment, and the high selectivity is desirable. For deeper lying and/or larger vessels, however, the near-infrared is the desirable wavelength. Deeper-lying vessels require wavelengths that are less efficiently absorbed by the dermis and epidermis. The light can penetrate to the depth of the vessels without being absorbed by melanin. Vessels having larger cross-sections also require near-infrared for more even cross-sectional heating. FIG. 4 shows that alexandrite laser light at 755 nm is better matched to absorption by both hemoglobin and oxy-hemoglobin than the common ruby laser light at 694 nm.

Figure 2:
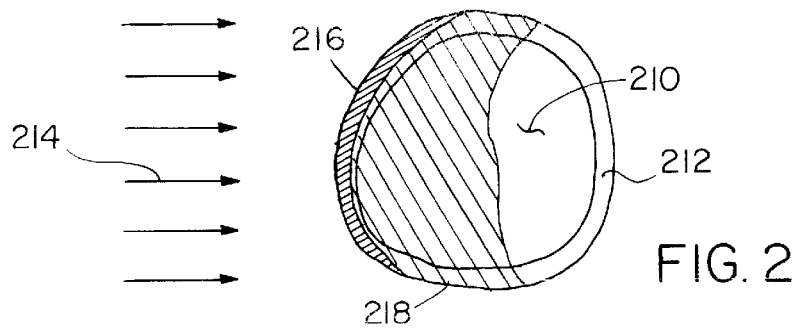
FIG. 2 shows a blood vessel cross-section and the different heating effects that are gained by using 577–585 nanometer light as opposed to near-infrared light.

FIG. 2 shows a blood vessel cross-section with an interior of the lumen 210 surrounded by the lumen's wall 212. For incident light indicated by arrows 214, the 577–585 nanometer range will be generally absorbed in a small region of the vessel's directly exposed wall (see reference numeral 216). For the larger vessels shown, this limits the area where the destructive effects of the light are realized. In contrast, when less efficiently absorbed near-infrared light is used, the region of heating 218 is expanded to cover a larger percentage of the interior 210 and also more of the vessel's walls 212. For larger vessels, this enlarged area is desirable. Specifically, the preferred light source is an alexandrite laser operating in the 755 nm range. Although, an alexandrite laser operating anywhere within its operational range of 710 to 810 nanometers could achieve some success. Filtered flashlamp light sources are also possible as are ruby, semiconductor diode, titanium-doped crystal, and Nd-doped crystal.

Returning to FIG. 1A, prior to irradiation, a thermal- or photo-sensitive irradiation marker is covered over the skin patch that is to be irradiated and that contains the unwanted vessels in step 115. This marker indicates to the operator those portions of the skin that have been exposed. The marker can be a temperature indicating liquid or stick that melts upon exposure to laser or the heat generated by it. One example is, OMEGALAQ™ produced by Omega Engineering, Incorporated although the bio-compatibility of this product has not been confirmed.

The use of a thermochromic or photochromic marker is useful when irradiating the skin with light in the near-infrared. When skin is exposed to light in the shorter frequencies, such as 577–585 nm, there is an instantaneous skin color change that acts as a record of those portions of the skin that have been treated. This effect does not occur when the skin is irradiated with the near-infrared. The use of the marker, which changes color or state for example in response to the light or induced heat, provides the helpful indication of those portions of the skin that have been treated.

The dermis containing the unwanted vessels is then irradiated using the selected wavelength, effective pulse duration, and fluence in step 116. Although a constant or near constant amplitude pulses may be used, the present invention preferably relies on pulse periodic heating techniques for longer pulse durations.

FIG. 3A is a plot of the power (P) supplied to the laser and the resulting temperature (T) of the targeted vessel as a function of time. A series of short pulses are generated, with a fractional duty cycle, for example, over the selected effective pulse duration Ts.

Pulse periodic heating techniques have certain advantages over constant amplitude heating shown in FIG. 3B, especially in flashlamp-excited lasers. A certain threshold of pump power Pth is needed to begin lasing in the gain media, the alexandrite, ruby, dye, or other media. The excess flashlamp power Pa over this lasing threshold then determines the amplitude of the laser output beam. By compressing the generated light into a series of shorter pulses, a higher percentage of the pumping power used to excite the media is realized in the energy of the output beam as shown by hatched regions in FIGS. 3A. In contrast, as shown in FIG. 3B, when operating the laser in a constant amplitude mode, most of the excitation power is consumed in reaching the lasing threshold. This power is lost to heat, increasing the need for liquid cooling and the demands on the power supply.

As also shown in FIGS. 3A and 3B, the heating induced in targeted tissue by the pulse periodic heating is only slightly different than that induced by the continuous amplitude heating. The tissue temperature increases in a stepwise fashion with pulse periodic heating as opposed to gradually in the continuous amplitude case. This difference in heating, however, does not affect the efficacy of the therapy because it is only the maximum temperatures that determine whether or not the vessels are destroyed.

Returning to FIG. 1A, the next step (118) is a waiting period or dwell time after the light therapy. This can be as short as 12 hours or as long as 6 months. The reason why this dwell time is necessary is not clear. It is theorized that this time allows the destructive effects of the light therapy to mature in the targeted vessels.

Finally, sclerotherapy is performed in step 120 on the vessels after the expiration of the dwell time. This is performed according to commonly known techniques in which a sclerosing agent is injected into the vessels. Preferred sclerosing agents include hypertonic saline and dextrose or and polidocanol (also known as Aetoxisclerol™). Lidocaine or other local anesthetic may be added to any of these solutions to assist in pain control. This is discussed in detail in *Sclerotherapy*, which is incorporated herein in its entirety by this reference.

FIG. 1B shows another embodiment of the combined light and sclerotherapy technique of the present invention. The second embodiment is similar to the technique disclosed in FIG. 1A insofar as the irradiation steps of 110–116 correspond to the irradiation steps of 126–134 in FIG. 1B. The second embodiment also implements a dwell time 124 and sclerotherapy is step 122. The difference here, however, is that the sclerotherapy 122 is performed before the irradiation in steps 126–134. The dwell time, step 124 follows the sclerotherapy 122 and then the irradiation 126–134.

Figures 5A, 5B:
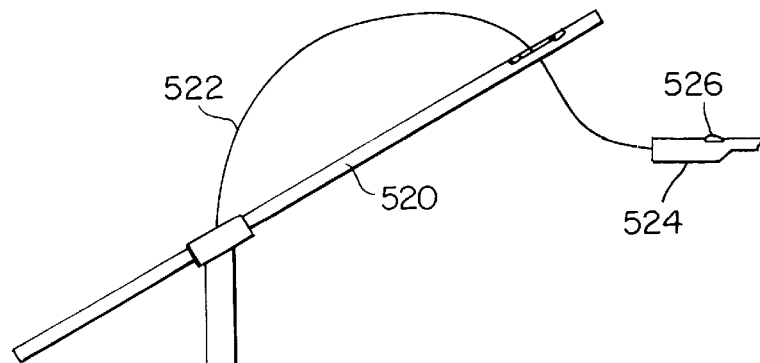
FIGS. 5A and 5B show two embodiments of a laser system for implementing the present invention in the form of a kit.

FIG. 5A shows a laser or flashlamp system that may be used to implement the inventive technique. It comprises a main unit 510 that has an alexandrite laser, ruby laser, filtered flashlamp, semiconductor diode laser, titanium-doped crystal laser, or Nd-doped crystal laser. A calibration port 512 and a front control panel 514 are also provided. A footswitch 516 is used for convenient control. A swing arm 520 holds the optical delivery fiber 522 that ends in a handpiece 524. The handpiece has a finger switch 526 also for activation. FIG. 5B shows another embodiment using an articulated arm 528 that is appropriate for a quartz fiber delivery system.

In the preferred embodiment, the laser system is a flashlamp-excited alexandrite laser system, without a Q-switching element to provide for long pulse durations. In the specific implementation, the partially reflecting mirror that defines the output aperture at one end of the laser's resonant cavity has a high reflectance of greater than 80%. Additionally, the resonant cavity is relatively short, 15 inches, or approximately 45 centimeters, with the defining mirrors having large radii of curvature forming a near concentric resonant cavity around the alexandrite crystal. The high beam divergence produced by this cavity is compensated for by using an optical delivery system that has a relatively large core diameter, between 1 and 1.5 millimeters. Other aspects of this laser are disclosed in U.S. Pat. application Ser. No. 08/744,344, filed Nov. 7, 1996, entitled "Alexandrite Laser System For Hair Removal And Method Therefor", by Horace W. Furumoto, et al., the teachings of which are incorporated herein by this reference in their entirety.

The laser system may be sold as part of a kit that includes an instruction manual that advises the combination of sclerotherapy with laser irradiation as shown in FIGS. 1A and 1B. The kit may also include the marker that shows were irradiation has been performed along with a sclerosing agent.

Figure 6:
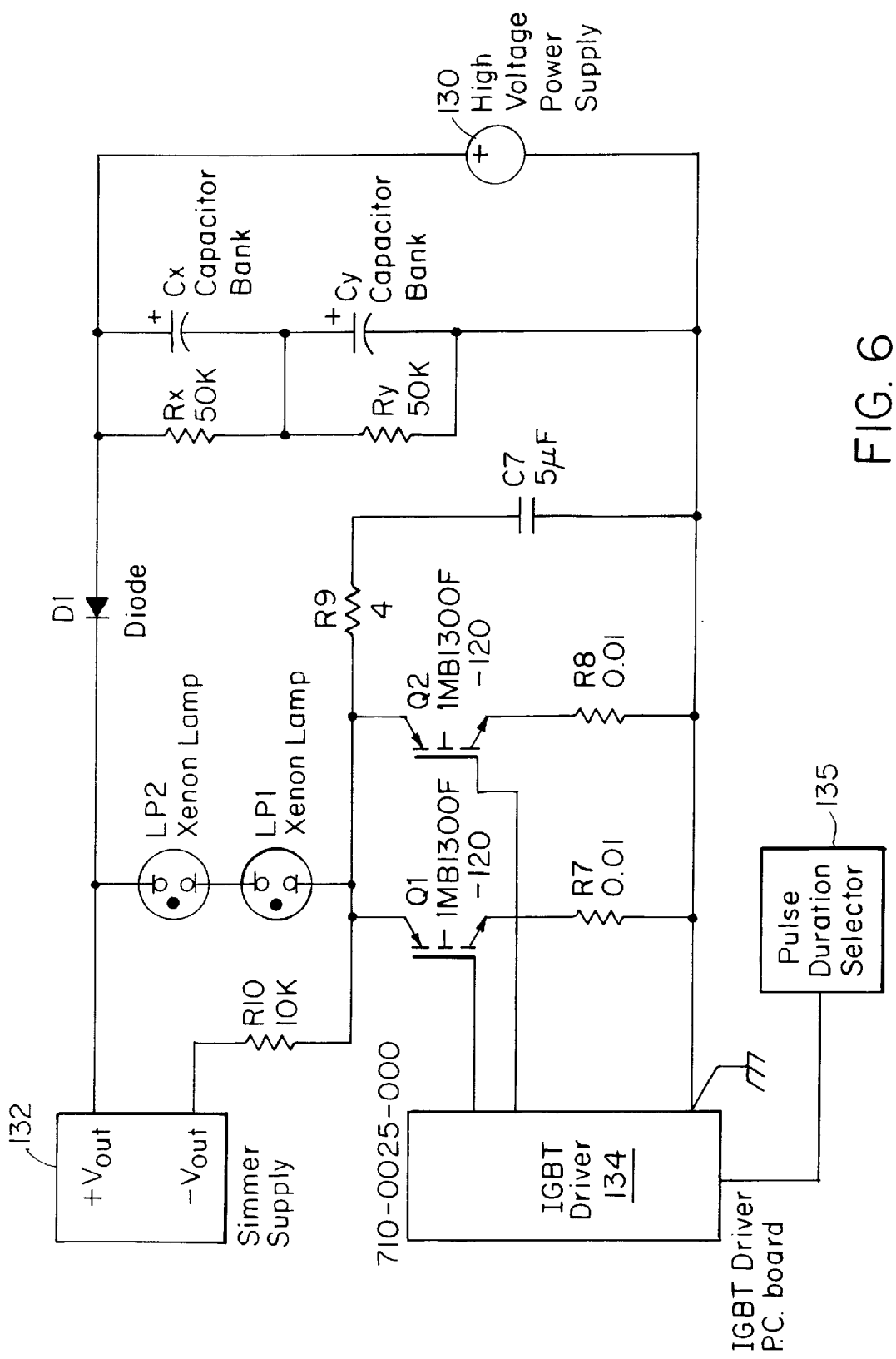
FIG. 6 is a circuit diagram showing an inventive flashlamp driver for the laser system.

FIG. 6 is a circuit diagram showing the flashlamp driver 122 for the laser system 510. Generally, the circuit has a simmer power supply 132 and a high voltage power supply 130 for two Xenon flashlamps, LP1 and LP2. As is known, the simmer supply 132 maintains the flashlamps LP1, LP2 at an operational temperature, so that when they are driven by the high voltage power supply, the light generation is virtually instantaneous. Two series capacitor banks, Cx, Cy, with parallel resistors Rx and Ry, respectively, are charged by the high voltage power supply to supplement the power provided to the flashlamps LP1, LP2 when pumping a preferably alexandrite gain media in the laser system 510.

Conventionally, laser flashlamps are driven by the high voltage power supply through a passive pulse-forming network (PFN). The present invention replaces this analog-style network with two IGBT transistors Q1,Q2 in an active PFN configuration. In operation, these transistors are normally in a non-conducting state. This connects the flashlamps, LP1 and LP2, only across the simmer power supply 132. When an IGBT driver 134, however, is signaled to initiate the generation of the laser light pulse, trigger signals are sent to both transistors Q1, Q2. This connects the series connected Xenon flashlamps LP1,LP2 to ground through resistors R7 and R8 and across the high voltage power supply 130. The flashlamps then draw current from both the high voltage power supply and the series capacitor banks Cx and Cy.

The use of transistors Q1,Q2 to connect the flashlamps across the high voltage power supply 130 has a number of advantages relative to prior art passive PFN circuits. First, with a passive PFN, it is generally difficult to provide for selection of the pulse duration; passive pulse-forming networks are generally tuned only to generate a pulse of a single duration. In contrast, the trigger pulse provided to the IGBT transistors Q1,Q2 may be easily digitally controlled via the IGBT driver 134, allowing any desired pulse duration consistent with the laser's characteristics and power supply. The only limitation on the pulse is the current the transistors Q1 and Q2 can conduct before they begin to be damaged. This factor, however, does not provide a hard upper limit to the pulse duration generated by the network since two or more transistors may be connected in parallel to meet the electrical current demands. Further, the use of the active PFN additionally allows for the use of pulse periodic heating techniques described above.

Experimental Results

A number of patients were treated first with a laser generating 5 msec pulses at 755 nm and then with sclerotherapy according to the following general protocol.

The area to be treated was identified and a template was placed to accommodate the group of veins to be treated in such a fashion that they could be easily identified. Anatomic landmarks and skin lesions were marked on the template so that placement could be accurately reproduced. Six punch-outs were then marked with a skin marking pen to "index" the photograph and the treatment cites. Two baseline photographs were taken. Sites were then treated with either 1) 15.0 J/cm$^2$, single pulse; 2) 15 J/cm$^2$, double pulse; 3) 20 J/cm$^2$, single pulse; 4) 20 J/cm$^2$, double pulse; and 30 J/cm$^2$, single pulse of radiation from the laser. After this treatment was performed, the patient was given a follow-up appointment in approximately 4 weeks.

At the second appointment, templates were again applied to the treatment site; the landmarks were matched; and the index marking holes were marked as well. Photographs were taken using the same protocol as in the first treatment session. The areas were again retreated using 20 J/cm$^2$ in a single or double pulse.

Some of the patients were treated again for a third time after another four week interval. This treatment was performed with the same protocol, in each case 20 J/cm$^2$ in two pulses was used.

In all the patients, sclerotherapy was performed within approximately 4 weeks from the last light-based therapy. In each case, 4–7 cc of 23.4% sterile, unpreserved saline solution mixed 30:1 with 2% Xylocaine was injected using a 30 gauge needle with a loupe assisted vision into any remaining spider veins.

Figure 7:
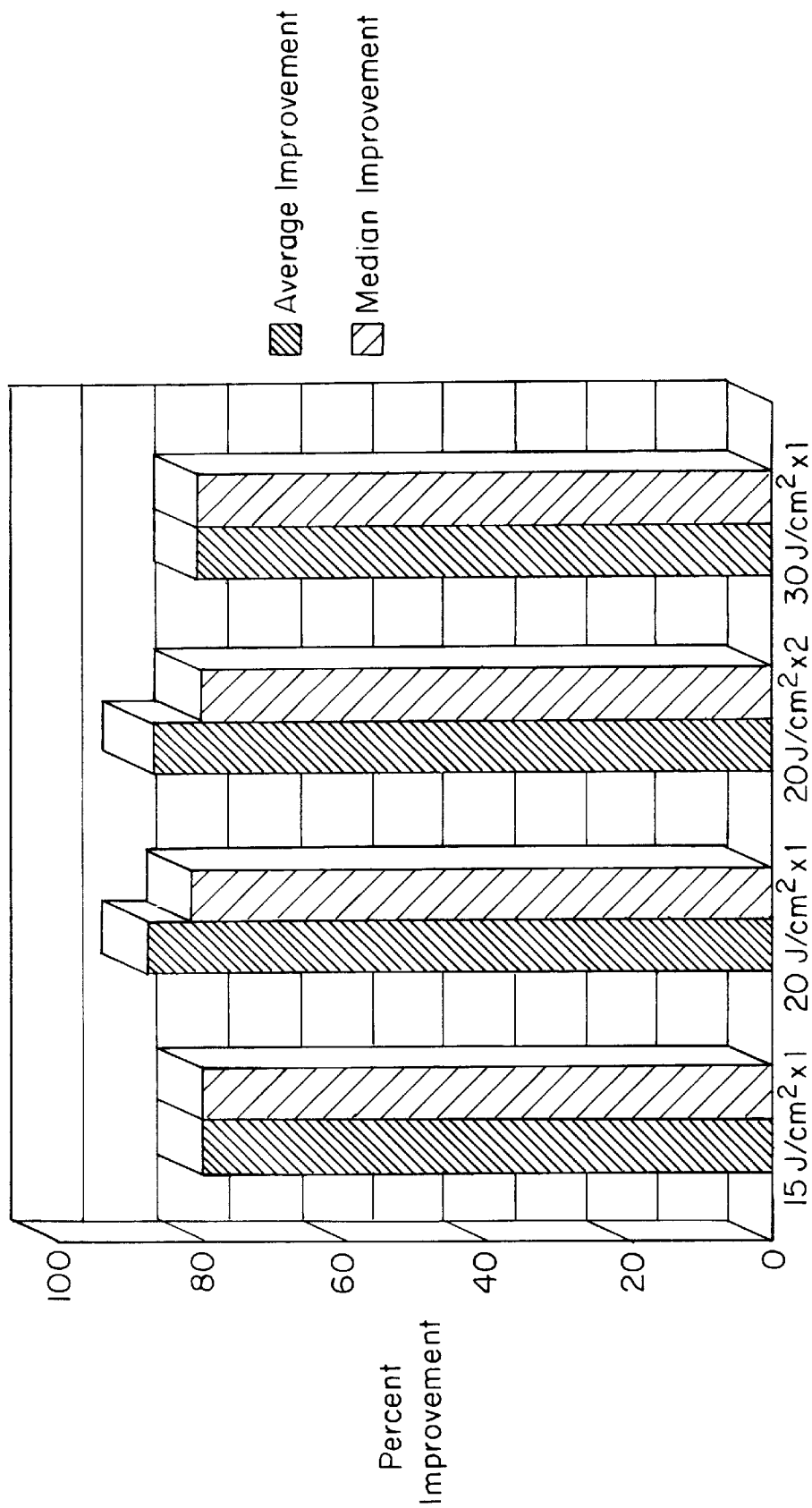
FIG. 7 is a graph illustrating the percent of leg vein elimination for various combinations of fluences and pulse combinations.

The general results of the limited study was that most patients showed greater than 76% clearing, with some patients exhibiting almost complete resolution of the veins. FIG. 7 summarizes the results for a number of different fluences included in the experiment, specifically 15 J/cm$^2$ single pulse, 20 J/cm$^2$ single pulse, 20 J/cm$^2$ double pulse, and 30 J/cm$^2$ single pulse. In each case, the average and median improvement exceeded 80%.

While this invention has been particularly shown and described with references to preferred embodiments thereof, it will be understood by those skilled in the art that various changes in form and detail may be made therein without departing from the spirit and scope of the invention as defined by the appended claims.

We claim:

1. A method for treating unwanted blood vessels, comprising:
    irradiating the vessels with light to denature the vessels or vessel walls;
    performing sclerotherapy on the vessels; and
    waiting for a dwell time of from 12 hours to 6 months between the irradiation of the vessels and the sclerotherapy.

2. The method described in claim 1, further comprising performing the step of irradiating the vessels prior to performing the sclerotherapy on the vessels.

3. The method described in claim 1, wherein the step of performing sclerotherapy comprises injecting a sclerosing agent into the vessels.

4. The method described in claim 3, wherein the sclerosing agent comprises a hypertonic saline solution.

5. The method described in claim 1, further comprising:
    observing the unwanted vessels for size;
    selecting a pulse duration for the irradiation based upon the observed size; and
    performing the irradiation for the selected pulse duration.

6. The method described in claim 5, wherein performing the irradiation comprises generating a series of separate light pulses over the selected pulse duration.

7. The method described in claim 1, further comprising:
    observing the unwanted vessels for depth;
    selecting a wavelength of the light based at least in part upon the observed depth; and
    performing the irradiation with light of the selected wavelength.

8. The method described in claim 1, wherein the step of irradiating the vessels comprises irradiating the vessels with near-infrared light.

9. The method described in claim 8, wherein performing the irradiation comprises generating a series of separate light pulses over a selected pulse duration.

10. The method described in claim 1, further comprising placing a marker on the skin prior to the irradiation to indicate portions of the skin that have been irradiated after the irradiation.

11. The method described in claim 1, further comprising performing the step of sclerotherapy prior to the step of irradiating the vessels.

12. The method described in claim 11, wherein the step of irradiating the vessels comprises irradiating the vessels with near-infrared light.

13. The method described in claim 1, further comprising irradiating vessels deeper than 1 millimeter.

14. A method for treating unwanted blood vessels, comprising:

observing the unwanted vessels for size;

selecting a pulse duration for the irradiation based upon the observed size;

irradiating the vessels with light of approximately 755 nm for the selected pulse duration to initiate destruction of the vessels;

waiting for a dwell time of between 12 hours and 6 months after the irradiation of the vessels to allow the effects of the irradiation to mature; and performing sclerotherapy on the vessels after the expiration of the dwell time.

* * * * *